United States Patent
Naas

Patent Number: 5,402,113
Date of Patent: Mar. 28, 1995

[54] METAL PARTICLE DETECTOR APPARATUS FOR NON-CONDUCTING FLUID SYSTEMS

[75] Inventor: David L. Naas, Concord, Calif.

[73] Assignee: AMOT Controls Corporation, Richmond, Calif.

[21] Appl. No.: 112,936

[22] Filed: Aug. 30, 1993

[51] Int. Cl.⁶ .............................................. G08B 17/10
[52] U.S. Cl. .................................... 340/631; 324/698; 200/61.09
[58] Field of Search ................. 340/631; 324/698, 693; 200/61.09

[56] References Cited

U.S. PATENT DOCUMENTS

| | | | |
|---|---|---|---|
| 2,689,277 | 9/1954 | Lidmalm | 340/631 |
| 3,373,352 | 8/1965 | Huigens | 200/61.09 |
| 3,422,417 | 2/1968 | Lowe | 340/631 |
| 3,686,926 | 8/1972 | Miller et al. | 324/698 |
| 4,030,028 | 6/1977 | Allender | 340/631 |
| 4,070,660 | 1/1978 | Tauber | 200/61.09 |
| 4,677,425 | 6/1987 | Singleton | 340/631 |
| 4,823,625 | 4/1989 | Hamilton | 340/631 |

*Primary Examiner*—Jeffery A. Hofsass
*Attorney, Agent, or Firm*—Henderson & Sturm

[57] ABSTRACT

A metal particle detector apparatus for use with flowing non-conductive fluid such as lubrication oil from an engine or other rotary device wherein the lubricated components include bearings or the like susceptible to failure, thereby placing harmful metal particles in the non-conductive fluid. A circuit grid comprising two electrodes affixed on a perforated electrically non-conductive plate which is disposed in the fluid flow in a manner which will catch the particles being carried by the fluid and when one, or an accumulation of these particles bridges the gap between electrodes completes an electrical circuit passing into the device from outside. In one embodiment, a primary and secondary seal are provided for sealing fluid against leaking into the electrical chamber leading to the electrical circuit or alarm system while still permitting the electrical circuit system to be electrically connected to the detector unit which is disposed in the flowing fluid. Compressible O-ring seals are used. A detector drain is provided for permitting the flow of fluid out of the housing of the detector if the primary seal begins to fail, acting first as a way to prevent oil from entering the chamber containing the electrical wiring for the alarm system and secondly as an indication to the user of when the detector seal is beginning to fail.

35 Claims, 4 Drawing Sheets

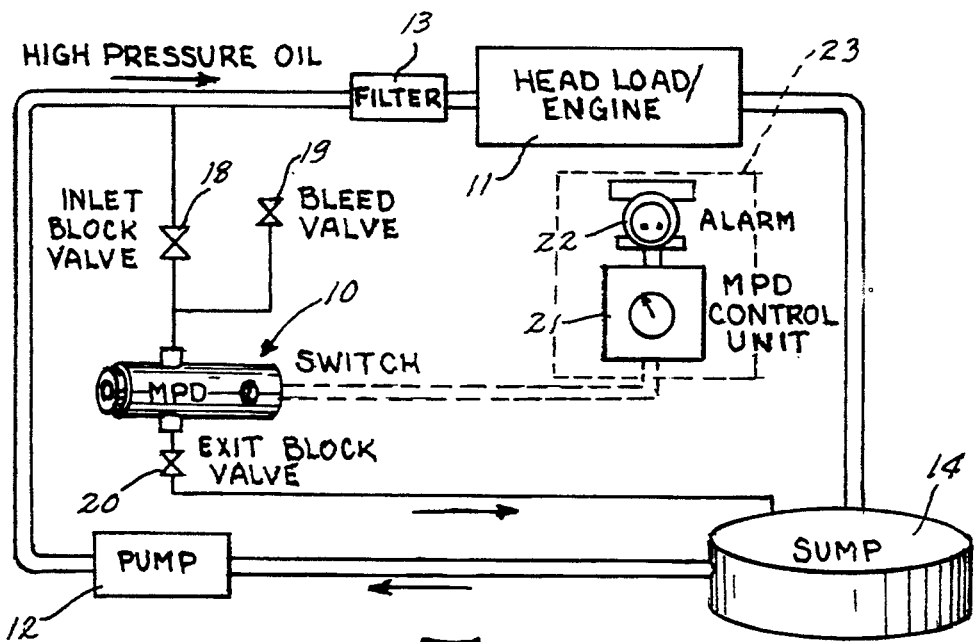
Fig. 1
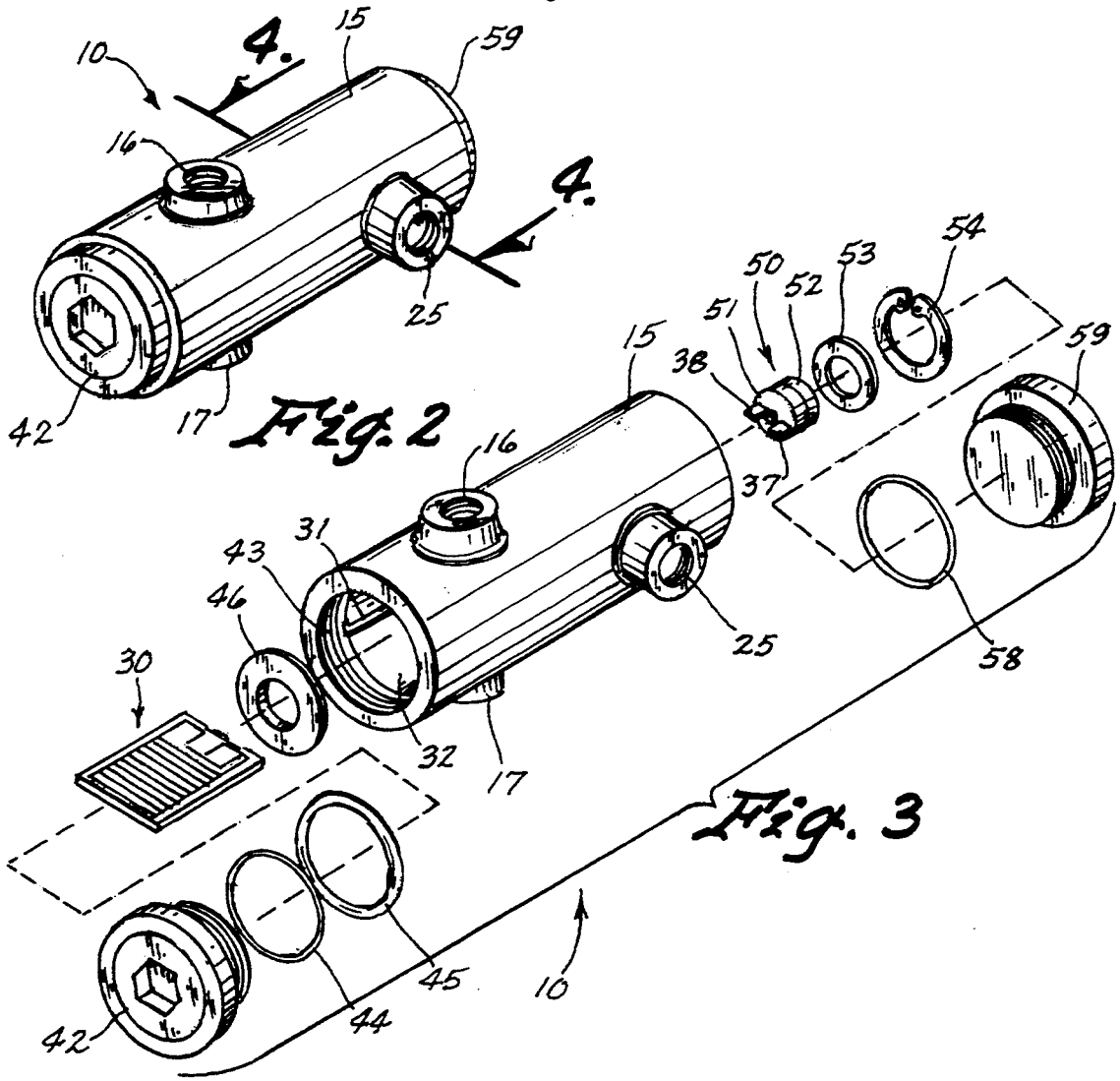
Fig. 2
Fig. 3

METAL PARTICLE DETECTOR APPARATUS FOR NON-CONDUCTING FLUID SYSTEMS

TECHNICAL FIELD

The present invention relates generally to a metal particle detector apparatus for non-conducting fluid systems and more particularly to an improvement to the system shown in U.S. Pat. No. 3,422,417.

BACKGROUND ART

Typically, a lubrication system is provided in most rotating machinery such as engines, turbines, pumps and the like. The non-conducting fluid such as lubricating oil is supplied to various wear points which are protected by bearings or other friction-reducing devices.

Prior to a total bearing failure and seizure of the rotating apparatus, small metal particles are emitted into the lubricating oil. Depending on the size of the rotating equipment, many variables of the lubrication system, (i.e. the metals of various bearing assemblies and other factors) determine how serious this problem is. The metal particles may be quite small or substantially large, and may vary in number from an occasional particle to a great number of particles, all of which can be indicative of failure conditions. In view of the great variety of circumstances, it will be understood and appreciated that a need has arisen for a metal bearing failure detector which is sensitive and responsive to particles of a given size or quantity, and which is not triggered by or responsive to a lesser number of particles in such circumstances.

U.S. Pat. No. 3,422,417 to Lowe, which is incorporated herein by reference, shows such a basic device which has been in use for many years. A problem with this prior art device is that if the insulation becomes hot and either melts out or is burned out because of a fire, or does not adhere properly, lubricating oil will leak into the electrical wiring cavity and the alarm system will fail. This problem is exacerbated because such failure can go undetected since it essentially disarms the alarm system without notification to the user. Consequently, the device being protected by the alarm system can essentially go undetected if the alarm system fails, and this of course can cause the primary equipment being protected, such as an engine, turbine, etc., to fail, at great expense to the user.

Consequently, there is a need for an improvement to the prior art metal particle detector devices such as that shown in the aforementioned Lowe patent to overcome the melting or burning insulation or adherence problem and to provide for early detection when the detector/alarm system is about to malfunction for this reason. If adhesion of the elastomeric seal is poor in the Lowe arrangement due to poor manufacturing processes, vibration during operation or high pressures may cause the seal to leak.

Additionally, there is considerable expense involved in the manufacture and insulation of the Lowe metal particle detector system because the metal plate detector unit must be insulated around the edges thereof. Accordingly, there is a need for a simpler and more dependable way of installing and using one of these detector units.

DISCLOSURE OF THE INVENTION

The present invention relates generally to a metal particle detector apparatus for use with flowing non-conducting fluids such as lubrication oil from an engine or other rotary device wherein the lubricated components include bearings or the like susceptible to failure, thereby placing harmful metal particles in the oil. A circuit grid comprising two electrodes affixed on a perforated electrically non-conductive plate which is disposed in the fluid flow in a manner which will catch the particles being carried by the fluid and when one, or an accumulation of these particles, bridges the gap between electrodes, it completes an electrical circuit passing into the device from the outside.

A double seal is provided for sealing the fluid against leaking into the electrical chamber while still permitting the electrical circuit system to be electrically connected to the detector unit which is disposed in the flowing fluid. A detector drain is provided for permitting the flow of fluid out of the housing of the detector if the seal assembly begins to fail, acting first as a way to prevent oil from entering the chamber containing the electrical wiring for the electrical circuit system and secondly as an indication to the user of when the detector seal is beginning to fail.

Another aspect of the present invention relates to the simplicity of installation of the detector units as compared to how it is done in the prior art.

An object of the present invention is to provide an improved metal particle detector apparatus for use in non-conducting fluid systems such as lubricating oil systems for engines, turbines, pumps or the like.

Another object of the present invention is to provide a metal particle detector of the aforementioned type which permits easy installation and replacement of a detector unit disposed within the flowing fluid.

A still further object of the present invention is to provide an improved sealing apparatus for the electrical system of such detector unit which does not require adhesion of an elastomeric seal.

A still further object of the present invention is to provide an oil drain for indicating when the seal assembly is in the process of failing and furthermore diverting the oil during such process of failure to the exterior of the housing to keep it away from the electrical system of an alarm unit or other electrical circuit device.

Other objects, advantages, and novel features of the present invention will become apparent from the following detailed description of the invention when considered in conjunction with the accompanying drawings.

BRIEF DESCRIPTION OF THE DRAWINGS

FIG. 1 shows a schematic view of a metal particle detector apparatus of the present invention used to protect a machine by detecting metal particles within the fluid being is circulated through it;

FIG. 2 is a perspective view of a preferred embodiment of the metal particle detector unit;

FIG. 3 is an exploded perspective view of the metal particle detector apparatus of FIG. 2;

BEST MODE FOR CARRYING OUT THE INVENTION

Figure 4:
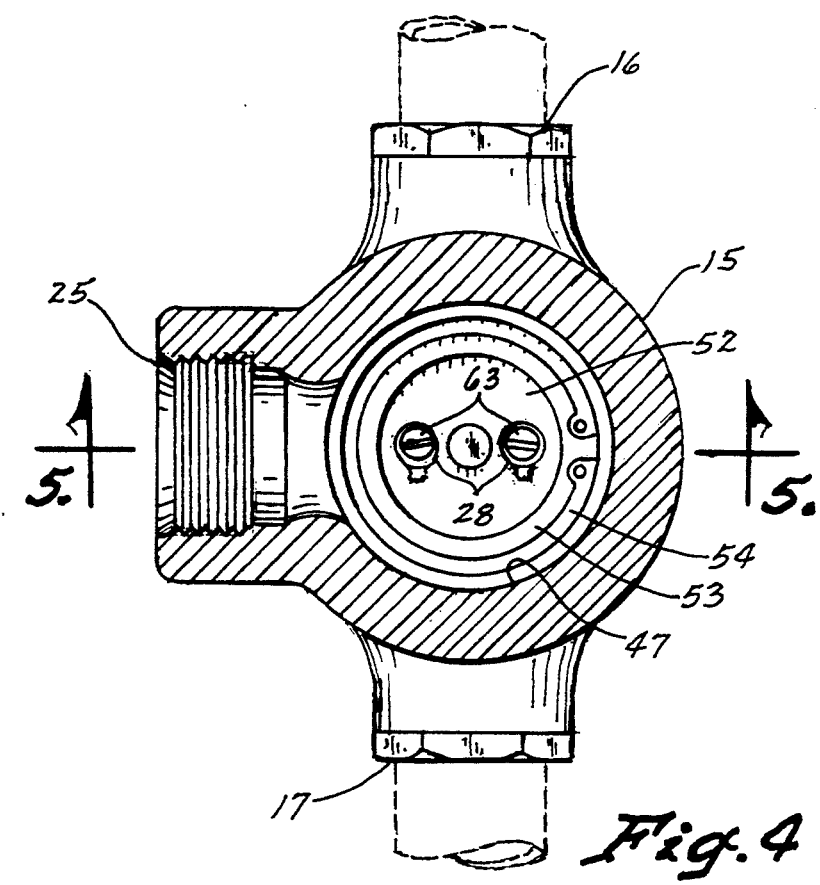
FIG. 4 is an enlarged cross sectional view taken along line 4—4 of FIG. 2.

Referring now to the drawings wherein like reference numerals designate identical or corresponding parts throughout the several views, the FIG. 1 example shows a metal particle detector control unit (10) connected into the lubricating oil circulatory system of an internal combustion engine (11). As is typical in such a system, there is a pump (12) which circulates oil through a filter (13) and through the engine (11). There is also a sump (14) for collecting the oil and providing a supply of oil to the pump (12). The metal particle detector control unit (10) includes an inlet opening (16) extending through housing (15) and an outlet opening (17).

An inlet block valve (18) and a bleed valve (19) are shown in the circuit of FIG. 1 for obvious reasons. Also an exit block valve (20) is provided and which can be used in conjunction with inlet block valve (18) and bleed valve (19) to permit easy installation of the metal particle detector or provide a way to close down the metal particle detector when desired, for example for inspection, if replacement is desired.

The metal particle detector control unit (10) is connected to the electrical control circuit (21) which may be connected to alarm (22) or relay output contacts.

Figure 5:
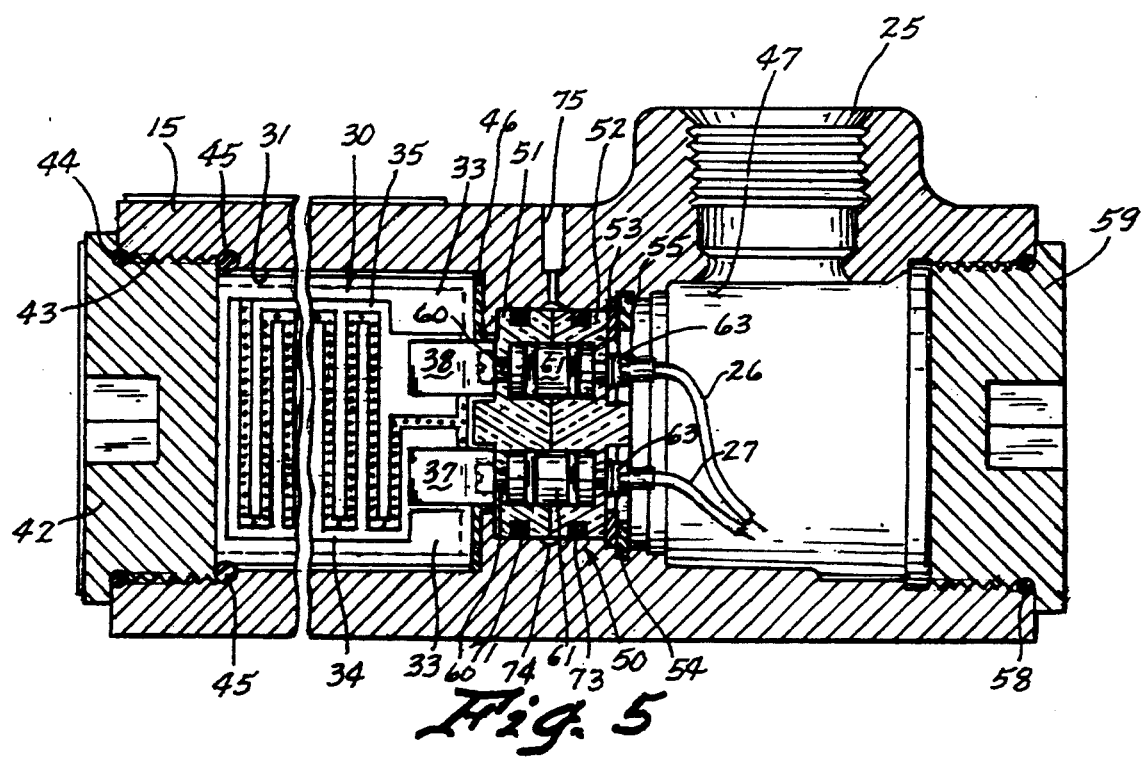
FIG. 5 is an enlarged cross sectional view taken along line 5—5 of FIG. 4.
Figure 6:
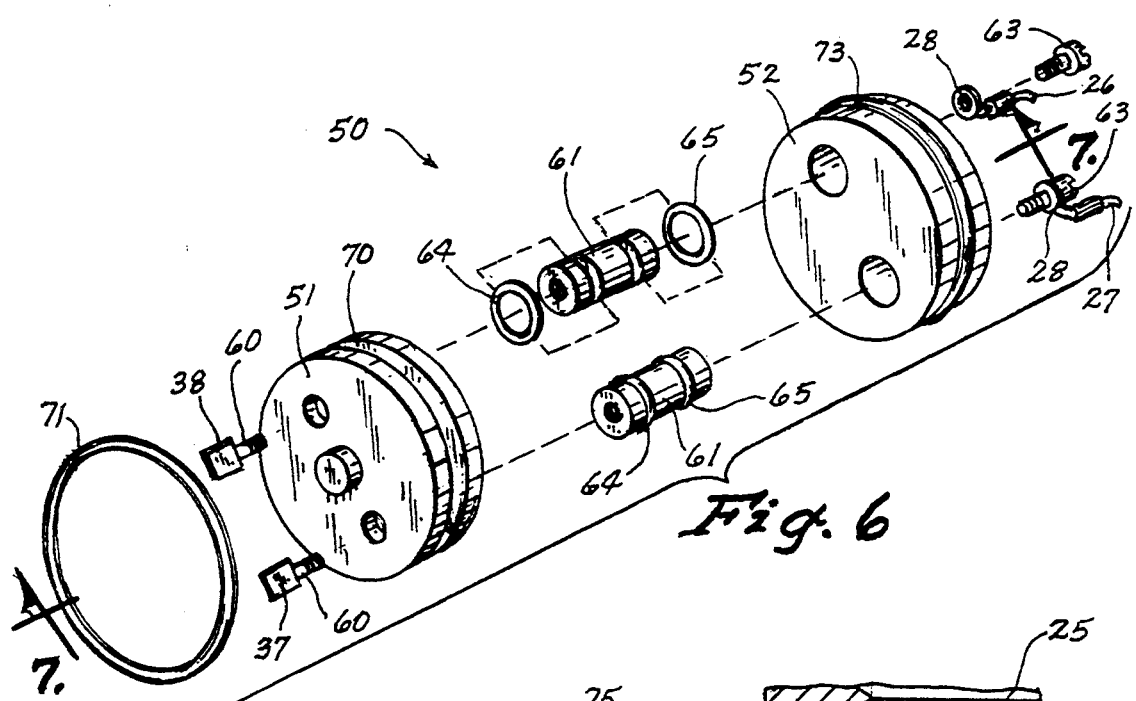
FIG. 6 is an exploded perspective view of the sealing apparatus which permits electricity to pass from the detector unit to an alarm system while sealing the oil flow chamber from the electrical compartment.

The housing (15) also includes an outlet opening (25) for providing a passage to protectively guide the alarm circuit wires (26) and (27) thereto as can readily be seen in FIG. 5.

Figure 8:
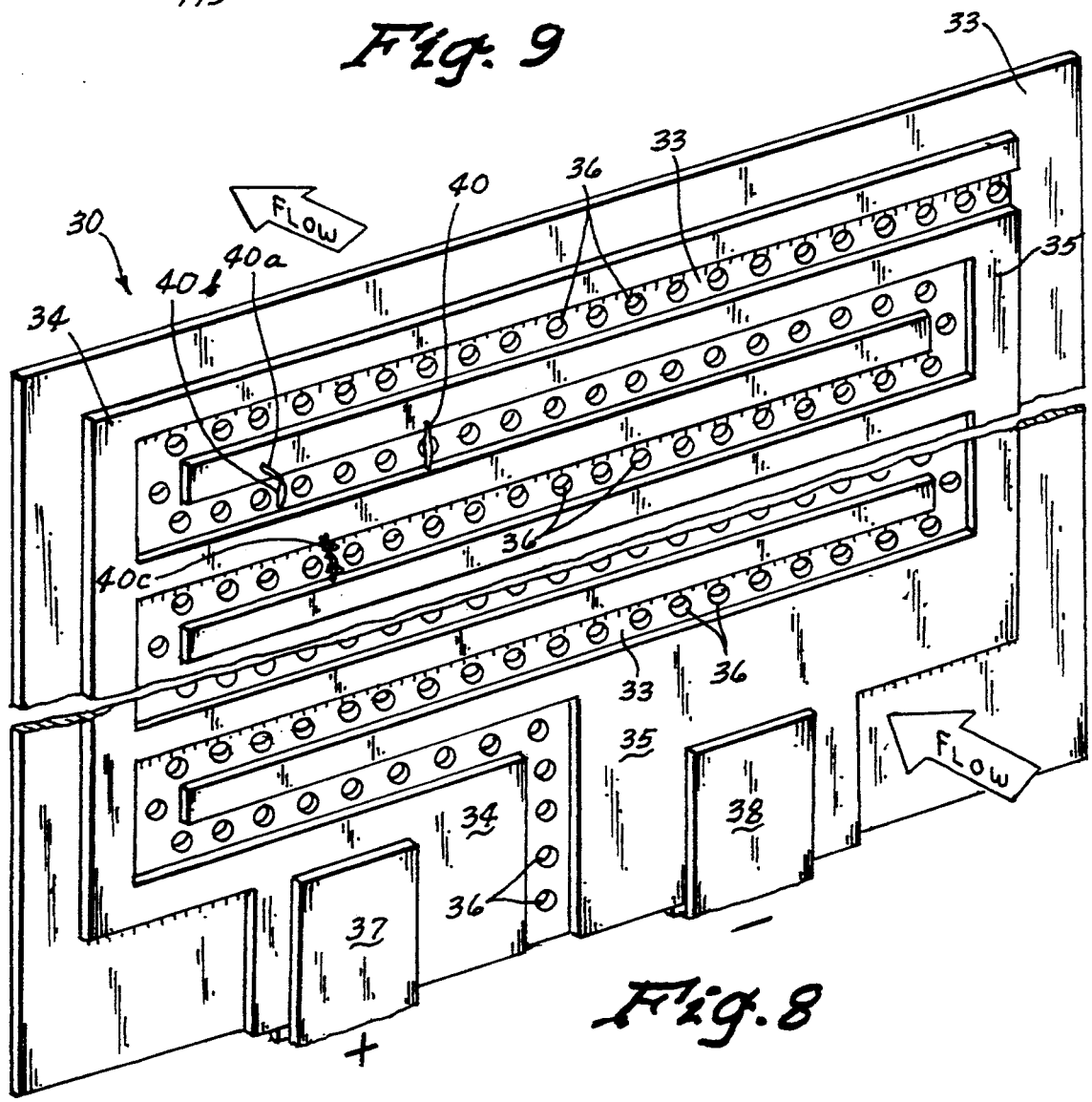
FIG. 8 is a perspective view of the main portion of the detector unit which permits the flow of oil therethrough but collects metal particles and signals the alarm when the metal particles bridge across between the positive and negative portions of the detector unit.

Referring to FIG. 3, a metal particle detector unit (30) is placed inside the housing (15) by slipping it into grooves (31) in each side of the interior of the housing chamber (32). This metal detector unit (30) can best be seen in FIG. 8 which shows an insulated portion (33) having metal or other conductive members (34) for providing a positive side of a circuit and a metal or other conductive member (35) for comprising the negative side of the circuit. The polarity can obviously be reversed if desired.

Holes (36) are disposed in the insulating non-conductive member (33) between the conductive members (34) and (35). Consequently, there is a space always between the conductive members (34) and (35) which essentially operates as an open switch which prevents the flow of electricity through the circuit. Clips (37) and (38) are connected to the conductive members (34) and (35), respectively. As will be explained later, when metal particles (40) bridge the gap between conductive members (34) and (35), this operates essentially like closing a switch between conductive members (34) and (35) and therefore completes the signal circuit (for example to an alarm) under certain conditions, depending upon the amount of electrical flow. Also, smaller members (40a) and (40b) can also serve to conduct electricity between conductive members (34) and (35) or an accumulation of smaller particles (40c) can also bridge the electrical gap between conductive members (34) and (35) as will be explained below.

Referring again to FIG. 3, it is noted that the detector (30) is held in the chamber (32) by a cap (42) which threadably engages the threads (43) in one end of the housing (15). Resilient O-ring seals (44) and (45) prevent oil from leaking out of the chamber (32) past the cap (42). The detector unit (30) also pushes against a resilient gasket (46) as is also shown in FIGS. 5 and 7.

Referring to FIG. 5, it is noted that an electrical chamber (47) is sealed from the oil flow chamber (32) by a primary and secondary seal unit (50) shown in FIG. 3, consisting of a first ceramic plug (51) and second ceramic plug (52). A washer (53) is abutted against member (52) and a spring-retaining member (54) is received in groove (55) in the housing (15) for securely holding the seal (50) against a front flange (56) in the housing (15), as also shown in FIGS. 5 and 7. This electrical chamber (47) is then sealed by an O-ring seal (58) and a cap (59), which is threaded into the other end of the housing (15) as shown in FIG. 5.

Figure 7:
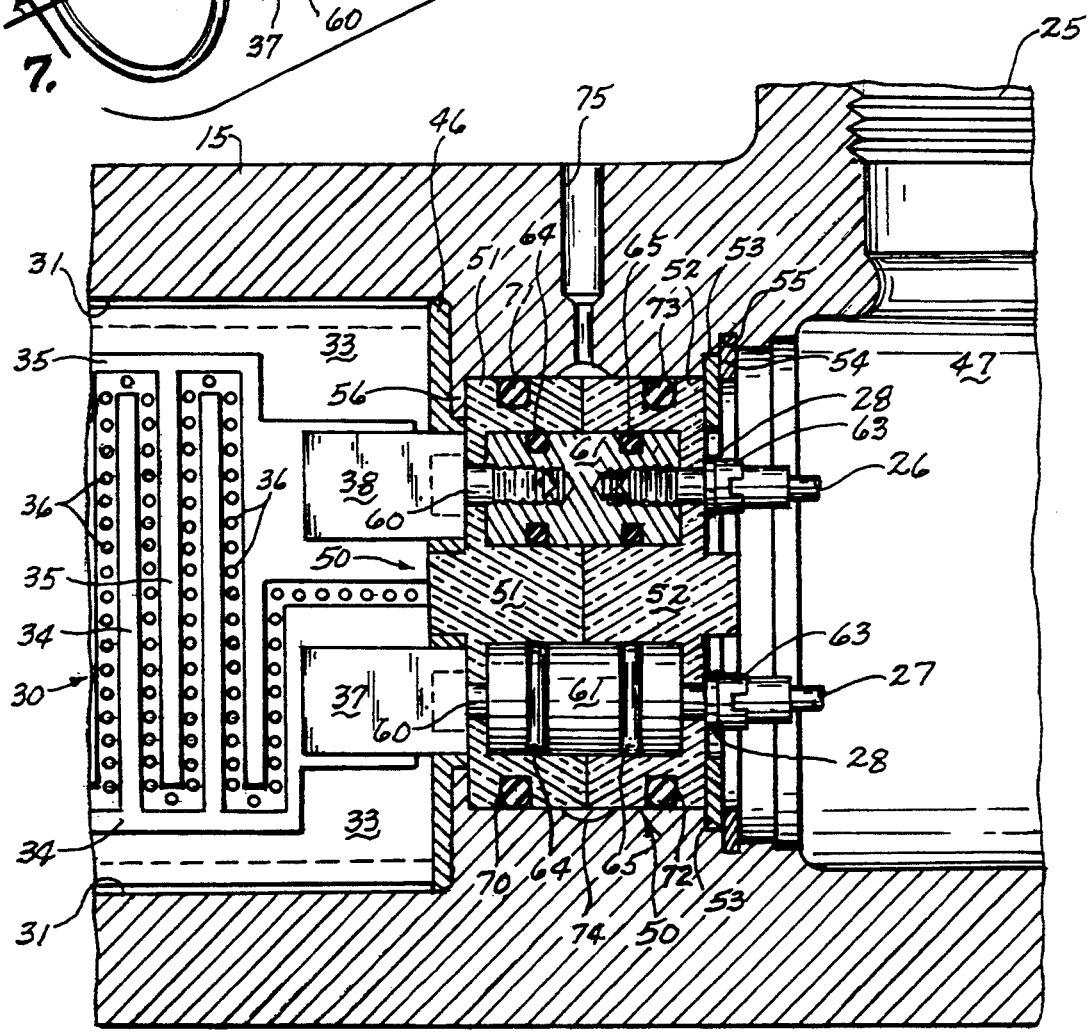
FIG. 7 is an enlarged partial cross sectional view of the seal assembly shown in FIGS. 5 and 6.

Once the unit is assembled as shown in FIGS. 5 and 7, it will be noted that the outer edge (33) of the insulated portion (33) is received in the grooves (31), but no electrical contact will be made since member (33) is an insulator. Conductor member (34) is bonded to the insulator member (33) and a conductor member (35) is also bonded to the conductor member (33), but as referred to above, these conductor members (34) and (35) are spaced apart by the portion of the insulator (33) having holes (36) therein. The opposite side of detector unit (30) is not shown, but is the same as the side shown, also with conductor members (34) and (35) bonded thereto in the same configuration and relationship as in the side shown.

The clip (37) connects to conductor (34) and conducts electricity through bolt (60), threadably engaged into brass conductor member (61). Wire (27), having connector (28) attached to one end thereof, is held to the brass connector (61) also by a bolt (63). The brass connector has O-ring seals (64) and (65) therearound in grooves in the brass connector (61). O-ring (64) is a primary seal and O-ring (65) is a secondary seal. For the sake of simplicity, the other brass connector, connected to clip (38) will also be numbered (60) since it is essentially a duplicate of the brass connector below it in FIGS. 5 and 7, and similarly, the other identical parts connected to the brass connector (61) will also be numbered identically, such as bolt (60), connector (28), bolt (63) and annular seals (64) and (65).

The seal (50) includes a ceramic or non-conductive material plug which has a main plug portion consisting of a first portion (51) and a second portion (52). The first and second portions (51) and (52) have a melting point higher than the temperature of burning oil. A first annular seal (71) extends in an annular groove (70) around the ceramic plug (51) and similarly, a second annular seal (73) extends in an annular groove (72) around ceramic plug (52). This provides primary and secondary seals.

An annular drain groove (74) extends around the plug or primary and secondary seals (50) where members (51) and (52) abut one another and passageways (74) and (75) lead to the exterior of the housing (15) as shown in FIGS. 5 and 7. FIG. 5 shows a standard connector (80)

which connects the wires (26) and (27) to alarm wires (86) and (87), respectively.

In operation, the engine of FIG. 1 will be protected because the lubricating oil being pumped therethrough also passes through metal particle detector control unit (10). Whenever a predetermined amount of electricity passes between metal detector plate (34) and (35), metal particles (40), (40a) and (40b) or metal particle accumulation (40c) or the like, this current can be fed into an optional metal particle control unit (21). Once a sufficient number of particles have been sensed, on the upstream side of the detector unit shown in FIG. 9, the completed electrical circuit may be used to indicate, alarm, or shut down the system. This will of course prevent any further damage to the engine until the problem can be solved, such as by replacing bearings or the like.

If any of the O-ring seals in the seal (50) fail and allow oil flow, this oil flow will pass out through annular channel (74) and ultimately to the outside of the housing (15) through passageways (75) and (76). This will alert the user that the seal (50) needs to be repaired and will, at the same time, prevent oil flow to the electrical compartment (47). This is important because the metal particle detector (MDP) could fail without the user's knowledge and the engine could unknowingly be operating unprotected by the alarm system. Failure of the seal (50) would constitute failure of the metal particle detector (30) because the oil would be flowing out of port (25) and around instead of through detector (30). What is shown in FIG. 5, i.e., electrical wires (26) and (27) and connectors (63), are essentially all that is in chamber (47). Furthermore, the oil flow through the outside not only keeps the oil out of the electrical chamber (47), but serves to warn the user that the primary seal needs to be repaired.

It will be appreciated that by using a detector unit which has electrical contacts only on one end thereof that the seal will not, and does not, need to make electrical contact along its two edges such as in the more expensive prior art device shown in U.S. Pat. No. 3,422,417 to Lowe. Furthermore, the grid (30) does not need to be through-plated to connect the top and bottom electrical passageways. Instead the oil flow of the pressure pushes the grid against the bottom side of the rails, and sensing occurs at the top where the particles land near openings (36).

Only the upstream side of insulated plate (33) is required to have conductor members (34) and (35) on it, but it is made with identical conductor members (34) and (35) on both sides so it will still work even if it is installed backwards.

In contrast, in the aforementioned Lowe patent, if the device became too hot, the seal could melt and oil would flow into the electrical cavity, thereby causing a malfunction of the alarm system without warning the user that the alarm system has been disarmed and potentially create a fire hazard. Instead, in one embodiment of the present invention (FIGS. 1–8) the present invention uses a non-melting and fire-resistant, non-combustible ceramic or non-conductive material in plugs (51) and (52) which would always block most of the flow. If resilient annular smaller seals (71) and (73) and (64) and (65) were to fail, they would allow only a small amount of oil flow. Because of the placement of these O-ring seals, the oil would flow out through non-pressurized port (75) instead of flowing into the electrical chamber (47). Consequently, even in the case of a fire or other meltdown, nearly all of the oil would flow to the outside of housing (15) through groove (74) and non-pressurized port (75).

Figure 9:
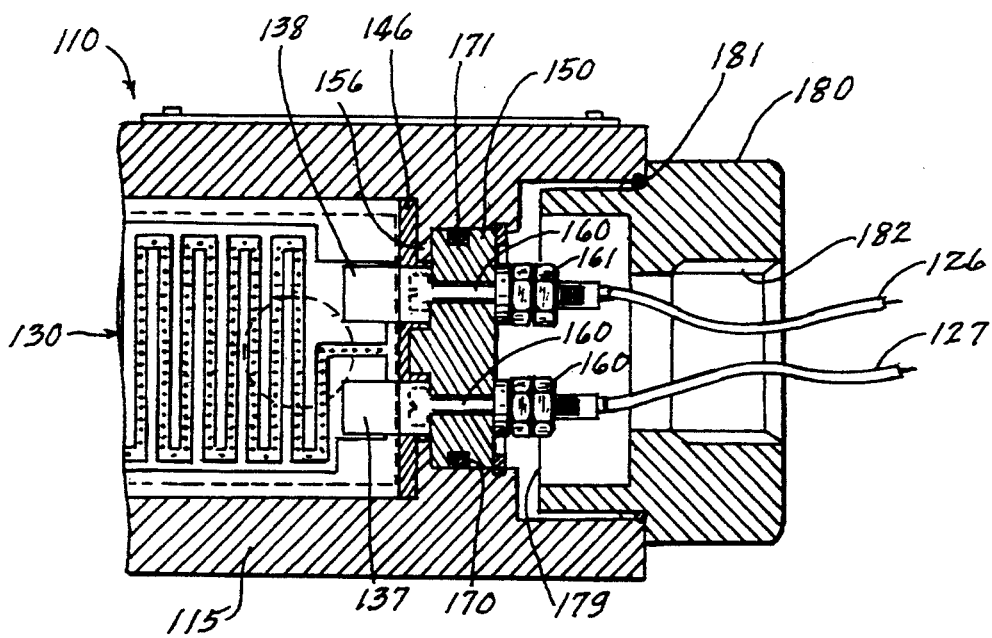
FIG. 9 is a cross sectional view of an alternate form of the invention similar to FIG. 7 of the above identified embodiment.

FIG. 9 shows an alternate form of the invention (110) which is essentially like the embodiment of FIGS. 2–8, except that it uses a single O-ring seal arrangement instead of a double seal arrangement. The body housing (115) includes inlet and outlet openings like those in FIGS. 4 and 5 and an opening which is closed by plug (150) and sealed by O-ring (171).

A metal particle detector unit (130) is inside housing (115) in grooves like aforementioned grooves (31) in each side of the interior of the housing chamber. The metal particle detector (130) can be identical to the one shown in FIGS. 2–8. Clips (137) and (138) connect to one end of the particle detector. Electrical connection is therefore made between one side of unit (130) through clip (138), bolt (160), nuts (161) to wires (126) which leads to an electrical circuit such as an alarm system. Similarly, clip (137) makes an electrical connection through plug (15) by connecting with bolt (160) and nuts (161) to wire (127), also leading to the electrical circuit.

The plug (150) can be constructed of meltable or non-fireproof materials such as a petroleum based plastic in order to save costs, but it can also be made of fire resistant and high melting point materials such as ceramic or epoxy materials.

Connector (180) fits in the electrical chamber (179) and opening (182) guides the wires (126) and (127) to the electrical circuit. O-ring seal (181) seals between connector (180) and housing (115).

Use of the plug (150) and resilient seal (171) is much more economical to produce and repair than the counterpart seal in the '417 Lowe patent, because the seal (50k) in the Lowe patent must adhere to both the housing (50) and the connector (64) in order to provide an adequate seal. O-ring (171) merely compresses to provide an adequate seal between plug (150) and body member (115).

Accordingly, it will be appreciated that the present invention does indeed accomplish the aforementioned objects. Obviously, many modifications and variations of the present invention are possible in light of the above teachings. It is therefore to be understood that, within the scope of the appended claims, the invention may be practiced otherwise than as specifically described.

I claim:

1. A metal detection apparatus cooperative with a flowing source of non-conductive fluid having metal particles therein on the occasion of a part failure, comprising:

a housing having a chamber therein;

connective means for permitting the flow of non-conductive fluid from a source through said chamber;

detection means for detecting metal particles;

means within said chamber for removably positioning said detection means generally transversely to the fluid flow through said chamber;

said detection means including conductive detector members extending over portions of the surface of said detection means facing the fluid flow, said conductive detector members being electrically insulated from each other and adapted to be contacted by metal particles in the fluid flowing through said chamber;

opening means associated with said detection means for directing oil flow past said detector members and for contacting metal particles thereagainst; and circuit means for providing an indication of contact of metal particles across said detector members, the improvement comprising:

at least a portion of said circuit means extending into said housing;

electrical conductor means connected to said detection means at one end thereof and to said circuit means at the other end thereof;

a passageway means having an interior surface thereon, said passageway means leading from said chamber to said circuit means for receiving said electrical conductor means therethrough; and seal means for sealing said passageway means to prevent flow of lubricating oil through said passageway means from said chamber while permitting the flow of electricity through said electrical conductor means, said sealing means including a primary seal and a compressed annular resilient seal member disposed between said primary seal and the interior surface of said passageway means in said housing.

2. The apparatus of claim 1 wherein said primary seal includes a main plug portion which is non-combustible.

3. The apparatus of claim 1 wherein a main plug portion of said seal means is constructed of a material with a melting point higher than the temperature of burning lubricating oil.

4. The apparatus of claim 2 wherein said apparatus further comprises:

a first conductive element disposed within said main plug portion;

first means for sealing said first conductive element to said main plug portion to prevent flow of lubricating oil therepast from said chamber;

a first electrical connector connecting one of said detector members to said first conductive element;

a second electrical connector connecting said first conductive element to said alarm circuit means;

a second conductive element disposed within said main plug portion;

second means for sealing said second conductive element to said main plug portion to prevent flow of lubricating oil therepast from said chamber; and a third electrical connector connecting the other of said detector members to said second conductive element; and a fourth electrical connector connecting said second conductive element to said alarm circuit means.

5. The apparatus of claim 4 wherein said main plug portion includes a first portion nearest to said detector members separable from a portion farther from said detector members and wherein said first and second conductive elements nest between said first and second portions of said main plug portion.

6. The apparatus of claim 5 wherein said first and second sealing means are disposed in the first portion of said main plug portion and including:

third means for sealing said first conductive element to said plug, said third sealing means being disposed in the second portion of said main plug portion; and fourth means for sealing said second conductive element to said main plug portion, said fourth sealing means being disposed in said second portion of said main plug portion.

7. The apparatus of claim 5 wherein a first primary annular seal extends around the outer periphery of said first portion of the main plug portion in said passageway means for operatively sealing against said housing; and a second secondary annular seal extends around the outer periphery of said second portion of the main plug portion in said passageway means for operatively sealing against said housing.

8. The apparatus of claim 7 including drain means disposed in said housing means from a point in said passageway means between said first primary and secondary annular seals for fluid communication to the outside of the housing means whereby if said primary annular seal fails, the lubricating oil will flow out through said drain means instead of flowing toward said electrical conductor means and further serving as an indicator that said annular primary seal has failed.

9. The apparatus of claim 1 including drain means disposed in said housing means from a point in said passageway means adjacent to the outer periphery of said primary seal to a place having a pressure lower than the pressure within said chamber whereby oil which leaks by said primary seal will pass into said drain means.

10. The apparatus of claim 9 wherein said place is outside of said housing.

11. The apparatus of claim 10 wherein said place is at ambient pressure.

12. The apparatus of claim 11 wherein said place is the outside of said housing.

13. The apparatus of claim 4 wherein said first, second, third and fourth electrical connectors are threadably attached to said respective conductive elements.

14. The apparatus of claim 13 wherein said first and second conductive elements are constructed of an electrically conductive material.

15. The apparatus of claim 1 wherein said electrical conductor means includes a pair of spring clip connectors in engagement with respective ones of said conductive detector members.

16. A metal detection apparatus cooperative with a flowing course of non-conductive fluid having metal particles therein on the occasion of a part failure, comprising:

a housing having a chamber therein;

connective means for permitting the flow of non-conductive fluid from a source through said chamber;

detection means for detecting metal particles;

means within said chamber for removably positioning said detection means generally transversely to the fluid flow through said chamber;

said detection means including a non-conductive plate member;

a first conductive detector member disposed on the upstream side of said nonconductive plate member;

a second conductive detector member disposed on the upstream side of said nonconductive plate member and spaced from said first conductive detector member so that they are not in electrical contact with each other;

openings disposed in and through said non-conductive plate member for permitting the flow of non-conductive fluid therethrough and thereby causing metal particles larger than said openings to accumulate between said first and second conductive detector members whereby an electrical current will flow through said accumulated metal particles between said first and second conductive detector members when a sufficient number or size of metal particles are present;

circuit means for providing an indication of contact of metal particles across said detector members, the improvement comprising:

at least a portion of said circuit means extending into said housing;

electrical conductor means, one end of said electrical conductor means being connected to only one end of said detection means and the other end of said electrical conductor means being connected to said circuit means whereby it is not necessary to provide electrical connectors along the sides of said detection means;

a passageway means leading from said chamber to said circuit means for receiving said electrical conductor means therethrough; and seal means for sealing said passageway means to prevent flow of lubricating oil through said passageway means from said chamber while permitting the flow of electricity through said electrical conductor means.

17. The apparatus of claim 16 including a pair of oppositely disposed grooves in said housing which form a part of said chamber and wherein respective side edges of said non-conductive plate members are disposed in said grooves for holding the plate member in a position to force a primary portion of the flow through said chamber to pass through the openings in said non-conductive plate member.

18. The apparatus of claim 17 wherein said sealing means includes a compressed annular seal member disposed between said seal means and said housing.

19. The apparatus of claim 16 wherein a main portion of said seal means is constructed of a material with a melting point higher than the temperature of burning lubricating oil.

20. The apparatus of claim 16 wherein said apparatus further comprises:

a first conductive element disposed within said main plug portion;

first means for sealing said first conductive element to a main plug portion of said seal means to prevent flow of lubricating oil therepast from said chamber;

a first electrical connector connecting one of said detector members to said first conductive element;

a second electrical connector connecting said first conductive element to said alarm circuit means;

a second conductive element disposed within said main plug portion;

second means for sealing said second conductive element to said main plug portion to prevent flow of lubricating oil therepast from said chamber; and a third electrical connector connecting the other of said detector members to said second conductive element; and a fourth electrical connector connecting said second conductive element to said alarm circuit means.

21. The apparatus of claim 20 wherein said main plug portion includes a first portion nearest to said detector members separable from a portion farther from said detector members and wherein said first and second conductive elements nest between said first and second portions of said main plug portion.

22. The apparatus of claim 21 wherein said first and second sealing means are disposed in the first portion of said main plug portion and including:

third means for sealing said first conductive element to said plug, said third sealing means being disposed in the second portion of said main plug portion; and fourth means for sealing said second conductive element to said main plug portion, said fourth sealing means being disposed in said second portion of said main plug portion.

23. The apparatus of claim 22 wherein a first primary annular seal extends around the outer periphery of said first portion of the main plug portion in said passageway means for operatively sealing against said housing; and a second secondary annular seal extends around the outer periphery of said second portion of the main plug portion in said passageway means for operatively sealing against said housing.

24. The apparatus of claim 23 including drain means disposed in said housing means from a point in said passageway means between said first primary and secondary annular seals for fluid communication to the outside of the housing means whereby if said primary annular seal fails, the lubricating oil will flow out through said drain means instead of flowing toward said electrical conductor means and further serving as an indicator that said annular primary seal has failed.

25. The apparatus of claim 16 including drain means disposed in said housing means from a point in said passageway means adjacent to the outer periphery of said primary seal to a place having a pressure lower than the pressure within said chamber whereby oil which leaks by said primary seal will pass into said drain means.

26. The apparatus of claim 25 wherein said place is outside of said housing.

27. The apparatus of claim 26 wherein said place is at ambient pressure.

28. The apparatus of claim 27 wherein said place is the outside of said housing.

29. The apparatus of claim 20 wherein said first, second, third and fourth electrical connectors are threadably attached to said respective conductive elements.

30. The apparatus of claim 29 wherein said first and second conductive elements are constructed of an electrically conductive material.

31. The apparatus of claim 16 wherein said electrical conductor means includes a pair of spring clip connectors in engagement with the first and second conductive detector members.

32. The apparatus of claim 18 wherein said seal means includes a plug which is constructed of a material which has a high degree of fire and melting resistance.

33. The apparatus of claim 32 wherein said plug is constructed of ceramic materials.

34. The apparatus of claim 33 wherein said plug is constructed of epoxy material.

35. The apparatus of claim 18 wherein said seal means includes a plug which is made of a combustible material which has a lower melting point than the melting point of ceramic or epoxy materials.

* * * * *